US009132271B2

(12) United States Patent
Kolen et al.

(10) Patent No.: US 9,132,271 B2
(45) Date of Patent: Sep. 15, 2015

(54) SYSTEM AND METHOD OF DELIVERING VESTIBULAR STIMULATION CUSTOMIZABLE TO INDIVIDUAL SUBJECTS

(75) Inventors: Alexander Franciscus Maria Kolen, Eindhoven (NL); Agathe Melanie Puszka, Fontaine (FR)

(73) Assignee: Koninklijke Philips N.V., Eindhoven (NL)

( * ) Notice: Subject to any disclaimer, the term of this patent is extended or adjusted under 35 U.S.C. 154(b) by 80 days.

(21) Appl. No.: 13/703,661

(22) PCT Filed: May 18, 2011

(86) PCT No.: PCT/IB2011/052189
§ 371 (c)(1),
(2), (4) Date: Dec. 12, 2012

(87) PCT Pub. No.: WO2011/161562
PCT Pub. Date: Dec. 29, 2011

(65) Prior Publication Data
US 2013/0090704 A1  Apr. 11, 2013

Related U.S. Application Data

(60) Provisional application No. 61/357,158, filed on Jun. 22, 2010.

(51) Int. Cl.
*A61N 1/36* (2006.01)
*A61N 1/04* (2006.01)
*A61N 1/05* (2006.01)

(52) U.S. Cl.
CPC .......... *A61N 1/36025* (2013.01); *A61N 1/0456* (2013.01); *A61N 1/0476* (2013.01); *A61N 1/36014* (2013.01); *A61N 1/0526* (2013.01); *A61N 1/36032* (2013.01)

(58) Field of Classification Search
CPC ............ A61N 1/36025; A61N 1/0476; A61N 1/36014; A61N 1/0456; A61N 1/0526; A61N 1/36032
USPC ....................................................... 607/2, 45
See application file for complete search history.

(56) References Cited

U.S. PATENT DOCUMENTS

| 6,077,237 A | 6/2000 | Campbell et al. |
| 6,301,500 B1 | 10/2001 | Van Herk et al. |

(Continued)

FOREIGN PATENT DOCUMENTS

| WO | 9952588 | 10/1999 |
| WO | 0066215 | 11/2000 |

(Continued)

OTHER PUBLICATIONS

T. M. Golaszewski et al; "Treatment of Hyperemesis Gravidarum by Electrical Stimulation of the Vestibular System", Journal of Psychosomatic Obstetrics and Gynecology, vol. 18, No. 3, pp. 244-246, 1997.

(Continued)

*Primary Examiner* — George Evanisko

(57) ABSTRACT

The vestibular system of a subject is stimulated in accordance with a therapy regime that dictates one or more parameters of the stimulation. The system is configured such that at a single site, one or more parameters of the stimulation varies for different locations at the site. This may enhance the customizability and/or effectiveness of the stimulation.

15 Claims, 4 Drawing Sheets

(56) References Cited

U.S. PATENT DOCUMENTS

| | | | |
|---|---|---|---|
| 6,314,324 B1 | 11/2001 | Lattner et al. | |
| 6,748,275 B2 * | 6/2004 | Lattner et al. | 607/42 |
| 6,909,917 B2 * | 6/2005 | Woods et al. | 607/46 |
| 8,041,429 B2 | 10/2011 | Kirby | |
| 8,145,318 B2 | 3/2012 | Van Herk | |
| 8,696,724 B2 * | 4/2014 | Rogers | 607/96 |
| 2003/0195588 A1 * | 10/2003 | Fischell et al. | 607/55 |
| 2006/0167524 A1 | 7/2006 | Kimura et al. | |
| 2007/0167985 A1 | 7/2007 | Kirby | |
| 2008/0097549 A1 | 4/2008 | Colbaugh et al. | |
| 2009/0082831 A1 | 3/2009 | Paul et al. | |
| 2012/0310303 A1 * | 12/2012 | Popovic et al. | 607/48 |

FOREIGN PATENT DOCUMENTS

| | | |
|---|---|---|
| WO | 03082104 A1 | 10/2003 |
| WO | 2007017778 A2 | 2/2007 |
| WO | 2007048087 A2 | 4/2007 |
| WO | 2008028063 A2 | 3/2008 |
| WO | 2009020862 A2 | 2/2009 |
| WO | 2009039294 A1 | 3/2009 |

OTHER PUBLICATIONS

F. Pusch et al; "Electrical Stimulation of the Vestibular System Prevents Postoperative Nausea and Vomiting", Acta Anaesthesiologica Scandinavica, vol. 44, No. 9, pp. 1145-1148, 2000.

* cited by examiner

SYSTEM AND METHOD OF DELIVERING VESTIBULAR STIMULATION CUSTOMIZABLE TO INDIVIDUAL SUBJECTS

The invention relates to the delivery of vestibular stimulation to a subject that is customizable to the anatomy and sensitivities of the subject.

Systems and methods of vestibular stimulation are known. For example, conventional systems and methods disclosed in U.S. Pat. Nos. 6,748,275 ("the '275 patent") and 6,314,324 ("the '324 patent") to Lattner et al. Various drawbacks and limitations associated with such known systems and methods exist.

For example, conventional systems configured to deliver vestibular stimulation only deliver a single electrical current to each side of the head. The current passes through an anode positioned on one side of the head to a cathode on the opposite side of the head. The intensity, frequency, and/or other properties of the stimulation provided by this current may be adjustable, however, the properties of the stimulation can only be adjusted for all of the stimulation provided to the head. There is no provision for varying the properties of electrical stimulation spatially at a single treatment site.

One aspect of the invention relates to a system configured to stimulate the vestibular system of a subject. In one embodiment, the system comprises a first set of subject contact surfaces and a processor. The first set of subject contact surfaces, includes subject contact that are spatially distinct from each other, and are configured to be installed on the skin of the subject at or near a first ear of the subject in electrical contact with the skin of the subject such that distribution of electrical stimulation to the first set of contact surfaces impacts the vestibular system of the subject on the same side of the subject as the first ear. The processor is configured to execute a power control module configured to control the distribution of electrical stimulation to the subject contact surfaces in the first set of subject contact surfaces individually such that at a given moment in time one or more parameters of the electrical stimulation distributed to the individual subject contact surfaces vary between different subject contact surfaces in the first set of subject contact surfaces.

Another aspect of the invention relates to a method of stimulating the vestibular system of a subject. In one embodiment, the method comprises contacting the skin of the subject through a first set of subject contact surfaces, wherein the subject contact surfaces in the first set of subject contact surfaces are spatially distinct from each other, and wherein the subject contact surfaces contact the skin of the subject at or near a first ear of the subject such that distribution of electrical stimulation to the first set of contact surfaces impacts the vestibular system of the subject on the same side of the subject as the first ear; and distributing electrical stimulation to the subject contact surfaces in the first set of subject contact surfaces individually such that at a given moment in time one or more parameters of the electrical stimulation distributed to the individual subject contact surfaces vary between different subject contact surfaces in the first set of subject contact surfaces.

Yet another aspect of the invention relates to a system configured to stimulate the vestibular system of a subject. In one embodiment, the system comprises first means for contacting the skin of the subject, wherein the subject contact surfaces in the first means for contacting contacts the skin of the subject at locations that are spatially distinct from each other and are at or near a first ear of the subject such that distribution of electrical stimulation to the locations contacted by the first means for contacting impacts the vestibular system of the subject on the same side of the subject as the first ear; and means for distributing electrical stimulation to individual ones of the locations on the skin of the subject contacted by the first means for contacting such that at a given moment in time one or more parameters of the electrical stimulation distributed to the individual locations vary between different locations.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn in proportion. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
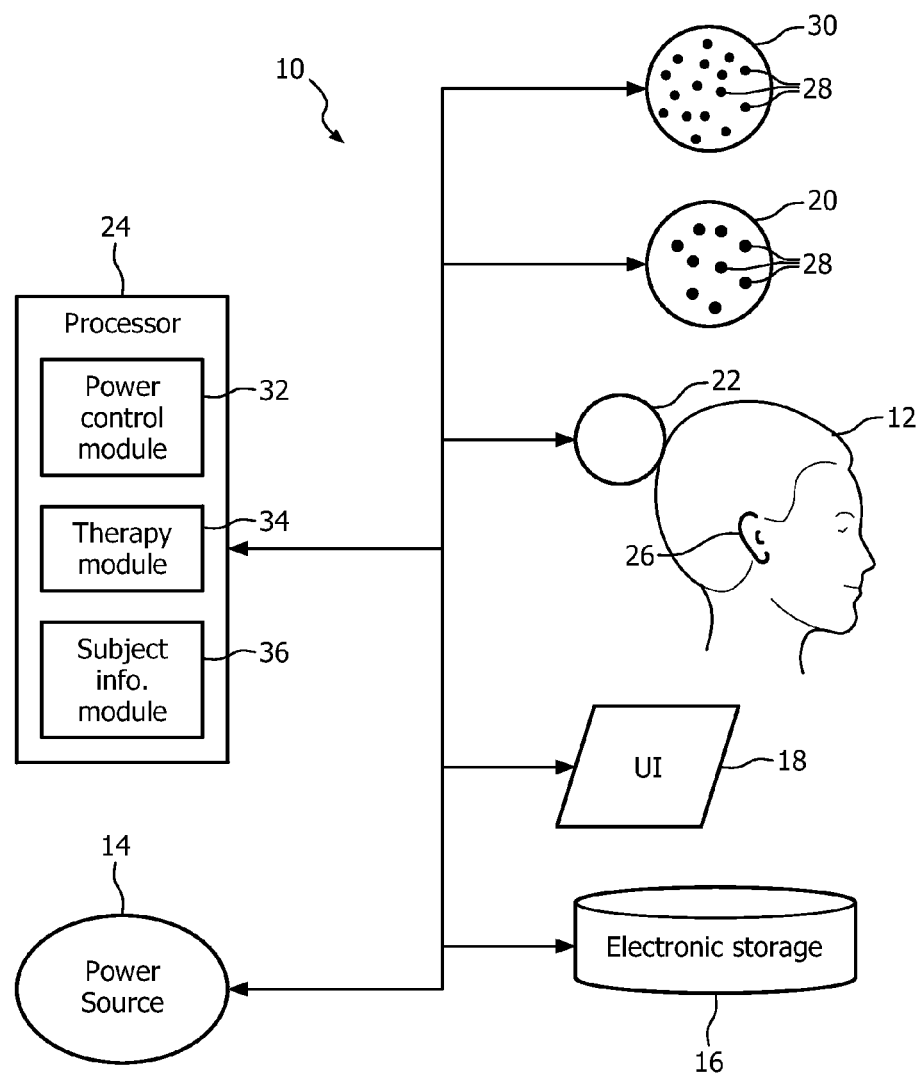
FIG. 1 illustrates a system configured to administer vestibular stimulation to a subject, according to one or more embodiments of the invention.

FIG. 1 illustrates a system 10 configured to administer vestibular stimulation to a subject 12. This involves stimulating the vestibular system of subject 12 in accordance with a therapy regime that dictates one or more parameters of the stimulation to have a therapeutic impact on the vestibular system of subject 12. For example, the therapy regime may be designed to impact the balance and/or spatial orientation of subject 12 to induce a rocking sensation, to reduce dizziness, and/or provide other impacts to the vestibular system. The therapeutic impact on the vestibular system of subject 12 may be intended to impact another physiological system through the vestibular system. For example, one or more functions of the hypothalamic system may be impacted by the stimulation of the vestibular system. For instance, U.S. application Ser. No. 11/581,670 ("the '670 application"), filed Oct. 16, 2006 describes the impact on the hypothalamic system that vestibular stimulation may have. The '670 application is hereby incorporated by reference into this application, in its entirety. In one embodiment, system 10 includes one or more of a power source 14, electronic storage 16, a user interface 18, a first subject stimulation interface 20, a sensor 22, a processor 24, and/or other components.

The power source 14 is configured to provide power to system 10 that is transmitted into the skin of subject 12 to stimulate the vestibular system of subject 12. The power source 14 may further provide power to power other components of system 10 (e.g., electronic storage 16, user interface 18, first subject stimulation interface 20, sensor 22, and/or power source 14). The power source 14 may include a fixed power source or a mobile power source. A fixed power source is a power source that is not portable (e.g., permanently fixed or inconvenient to move in the context of system 10). For example, a fixed power source could include one or more of a wall socket, a large generator, and/or other fixed power sources. A mobile power source is a power source that is portable within the context of the use of system 10. For example, a battery or capacitor could easily be carried with one or more other components of system 10.

In one embodiment, electronic storage 16 comprises electronic storage media that electronically stores information. The electronic storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 24, information received via user interface 18, information received from sensor 22, and/or other information that enables system 10 to function properly. Electronic storage 16 may be a separate component within system 10, or electronic storage 16 may be provided integrally with one or more other components of system 10 (e.g., processor 24).

User interface 18 is configured to provide an interface between system 10 and a user (e.g., subject 12, a caregiver, a therapy decision maker, a researcher, and/or other users) through which the user may provide information to and receive information from system 10. This enables data, results, and/or instructions and any other communicable items, collectively referred to as "information," to be communicated between the user and processor 24, and/or other components of system 10. Examples of interface devices suitable for inclusion in user interface 18 include a keypad, buttons, switches, a keyboard, knobs, levers, a display screen, a touch screen, speakers, a microphone, an indicator light, an audible alarm, a printer, and/or other interface devices. In one embodiment, user interface 18 actually includes a plurality of separate interfaces.

It is to be understood that other communication techniques, either hard-wired or wireless, are also contemplated by the present invention as user interface 18. For example, the present invention contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

The first subject stimulation interface 20 is configured to distribute electrical stimulation into the skin of subject 12 such that the parameters of the electrical stimulation vary at a given point in time as a function of position on the skin of subject 12. The first subject stimulation interface 20 is configured to distribute electrical stimulation into the skin of subject 12 at or near a first ear 26 of subject 12 such that distribution of electrical stimulation impacts the vestibular system of subject 12 on the same side of subject 12 as first ear 26. As used herein, "at or near first ear 26" of subject 12 may include an area within about within about 10 cm of first ear 26. It will be appreciated that this distance is not intended to be limiting. For example, in one embodiment "at or near first ear 26" may refer to an area within about 5 cm of first ear 26.

In one embodiment, first subject stimulation interface 20 includes a set of subject contact surfaces 28. As can be seen in FIG. 1, subject contact surfaces 28 are spatially distinct from each other. The first subject stimulation interface 20 is configured to be installed on subject 12 at or near first ear 26 such that subject contact surfaces 28 contact spatially distinct locations on the skin of subject 12 at or near first ear 26. The subject contact surfaces 28 are formed from an electrically conductive material in order to communicate electrical stimulation into the skin of subject 12. The first subject stimulation interface 20 may include a mechanism for affixing subject contact surfaces 28 to the skin of subject 12. For example, first subject stimulation interface 20 may include an adhesive that removably adheres first subject stimulation interface 20 to the skin of subject 12.

The subject contact surfaces 28 may be used to measure electrical skin properties of subject 12. The subject contact surfaces 28 may generate output signals conveying information related to electrical skin properties at the locations at which they are installed on subject, and/or information related to body tissue electrical properties between different combinations of the locations at which subject contact surfaces 28 are installed on subject 12. As is discussed further below, these output signals, and/or information derived therefrom, can be used as input to in determining and/or tuning the distribution of electrical stimulation among subject contact surfaces 28 to achieve a particular therapeutic effect on the vestibular system of the subject 12. The generation of such output signals by subject contact surfaces 28 and/or the manner in which information related to electrical skin and/or body tissue properties can be derived from the output signals may be found, for example, in one or more of U.S. Pat. No. 6,301, 500 ("the '500 patent"), U.S. patent application Ser. No. 10/509,239 ("the '239 application"), and/or U.S. patent application Ser. No. 11/997,783 ("the '783 application"). The '500 patent, the '239 application, and the '783 application are hereby incorporated by reference into this disclosure in their entirety.

In one embodiment, first subject stimulation interface 20 is a single component, as shown in FIG. 1, that carries subject contact surfaces 28 thereon. In one embodiment, first subject stimulation interface 20 includes a plurality of separate components, each carrying one or more of subject contact surfaces 28 in the first set of subject contact surfaces 28.

In one embodiment, system 10 further includes a second subject stimulation interface 30. It will be appreciated that this is not intended to be limiting, as the scope of this disclosure includes embodiments in which second subject stimulation interface 30 is not included. The second subject stimulation interface 30 is configured to distribute electrical stimulation into the skin of subject 12 such that the parameters of the electrical stimulation vary at a given point in time as a function of position on the skin of subject 12. The second subject stimulation interface 30 is configured to distribute electrical stimulation into the skin of subject 12 at or near a second ear of subject 12 (not shown in FIG. 1) such that distribution of electrical stimulation impacts the vestibular system of subject 12 on the same side of subject 12 as the second ear. The second subject stimulation interface 30 includes a second set of subject contact surfaces 28 that function in substantially the same manner as the first set of subject contact surfaces 28 described above. However, the second set of subject contact surfaces 28 are carried by second subject stimulation interface 30 for installation at or near the second ear of subject 12.

The system 10 may include other subject stimulation interfaces. For example, one or more electrodes configured for attachment to the back of the neck of subject 12, the back of subject 12, an appendage of subject 12 (e.g., arm, leg, and/or other appendages), and/or other body parts of subject 12.

The sensor 22 is configured to generate an output signal (or output signals) conveying information related to the communication of electrical stimulation between at least one of subject contact surfaces 28 and the skin of subject 12 and/or related to the impact on the vestibular system of electrical stimulation distributed into the skin of subject 12 by first subject stimulation interface 20 and/or second subject stimulation interface 30. For example, the output signal generated by sensor 22 may convey information related to the resistance, capacitance, impedance, and/or other electrical properties of subject 12 at or near the locations contacted by the first and/or second set of subject contact surfaces 28. The output signals generated by sensor 22 may convey information related to physiological function that is impacted (directly or indirectly) by stimulation of the vestibular system. Such physiological function may include one or more of a vascular tone, a core temperature, a metabolic function, a pulse shape, a galvanic skin response, a heart rate variability, a baroreceptor sensitivity, a body weight, a muscle sympathetic nerve activation, a pupillary dilation, peristaltic movement of materials through the patient's digestive system, a blood pressure, oxygenation, hydration, respiration, and/or other physiological function. The output signals generated by sensor 22 may convey information related to the impact on balance and/or spatial orientation of the electrical stimulation. For example, sensor 22 may include an accelerometer, a gyroscope, a digital compass, and/or other sensors that generate output signals conveying information related to the position and/or motion of subject 12.

In one embodiment, one or more subject contact surfaces 28 are considered to also provide some of the functionality attributed herein to sensor 22. For example, subject contact surfaces 28 may generate output signals conveying information related to electrical skin and/or body tissue properties at or near one or both of subject stimulation interfaces 20 and/or 30. This was discussed above in the description of subject contact surfaces 28. For convenience, references in this disclosure to sensor 22 may refer not only to sensors separate from subject contact surfaces 28, but also and/or instead to one or more subject contact surfaces 28 of first subject stimulation interface 20 and/or second subject stimulation interface 30 being used to measure electrical properties of subject 12.

It will be appreciated that the illustration in FIG. 1 of sensor 22 as a single component is not intended to be limiting. In one embodiment, sensor 22 includes a plurality of sensors. The plurality of sensors may be co-located on a single physical device, or the plurality of sensors may be distributed between different devices. In one embodiment, sensor 22 includes at least one sensor unit disposed on subject 12 at or near first ear 26 and at least one sensor unit disposed on subject 12 at or near the second ear.

Processor 24 is configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device, or processor 24 may represent processing functionality of a plurality of devices operating in coordination.

As is shown in FIG. 1, processor 24 may be configured to execute one or more computer program modules. The one or more computer program modules may include one or more of a power control module 32, a therapy module 34, a subject information module 36, and/or other modules. Processor 24 may be configured to execute modules 32, 34, and/or 36 by software; hardware; firmware; some combination of software, hardware, and/or firmware; and/or other mechanisms for configuring processing capabilities on processor 24.

It should be appreciated that although modules 32, 34, and 36 are illustrated in FIG. 1 as being co-located within a single processing unit, in implementations in which processor 24 includes multiple processing units, one or more of modules 32, 34, and/or 36 may be located remotely from the other modules. The description of the functionality provided by the different modules 32, 34, and/or 36 described below is for illustrative purposes, and is not intended to be limiting, as any of modules 32, 34, and/or 36 may provide more or less functionality than is described. For example, one or more of modules 32, 34, and/or 36 may be eliminated, and some or all of its functionality may be provided by other ones of modules 32, 34, and/or 36. As another example, processor 24 may be configured to execute one or more additional modules that may perform some or all of the functionality attributed below to one of modules 32, 34, and/or 36.

The power control module 32 is configured to control the distribution of electrical stimulation to subject contact surfaces 28 individually. This is accomplished by controlling the power delivered from power source 14 to the individual subject contact surfaces 28 on a surface by surface basis. This enables power control module 32 to control electrical stimulation delivered by the first set of subject contact surfaces 28 such that at a given point in time one or more parameters of the electrical stimulation delivered by the first set of subject contact surfaces 28 varies between different ones of the subject contact surfaces 28 in the first set of subject contact surfaces 28. The one or more parameters may include one or more of amplitude, frequency of modulation, phase of modulation, polarity, pulse shape of modulation, pulse width of modulation, pulse pause of modulation, pulse train of modulation, and/or other parameters. This enhances the functionality of first subject stimulation interface 20 and/or second subject stimulation interface 30 in delivering electrical stimulation to subject 12 with respect to conventional vestibular stimulation systems including electrodes distributing electrical stimulation to the skin of subject 12. For example, conventional systems generally include a single electrode on each side of the head of subject 12, and/or do not enable parameters of electrical stimulation to be varied by position at a single stimulation delivery site (e.g., such as the area covered by first subject stimulation interface 20 or second subject stimulation interface 30).

The therapy module 34 is configured to provide a therapy regime to power control module 32. The therapy regime dictates the manner in which power should be distributed to the individual ones of subject contact surfaces 28 in a coordinated manner to have therapeutic impact on the vestibular system. The therapy module 34 may access the therapy regime from a plurality of therapy regimes (e.g., previously stored to electronic storage 16). One or more settings of electrical stimulation parameters dictated by the therapy regime may be configured based on user selection (e.g., via user interface 18). The therapy regime itself may be selected from a plurality of potential regimes based on user selection (e.g., via user interface 18).

The subject information module 36 is configured to receive information from sensor 22 and/or subject contact surfaces 28, and to determine information related to the therapy being received by subject 12 in the form of vestibular stimulation. Such information may include one or more parameters related to the distribution of electrical stimulation into the skin of subject 12. Such parameters may include one or more of resistance, capacitance, impedance, and/or other parameters. The information determined by subject information module 36 may include an impact of the vestibular stimulation being administered to subject 12 on one or more physiological functions of subject 12. The one or more physiological functions may include one or more of balance or spatial orientation (based on a position or motion sensor signal), a vascular tone, a core temperature, a metabolic function, a pulse shape, a galvanic skin response, a heart rate variability, a baroreceptor sensitivity, a body weight, a muscle sympathetic nerve activation, a pupillary dilation, peristaltic movement of materials through the patient's digestive system, a blood pressure, and/or other physiological functions.

The impact of electrical stimulation applied to the external skin of a subject for the purpose of stimulating the vestibular system (e.g., in the manner of system 10) has been found to vary significantly from subject to subject. Probable reasons for this difference in impact include differences in anatomy, differences in electrical properties between subjects, security of the contact between the surfaces through which electrical stimulation is applied and the skin of the subject, and/or other differences between subjects. Further, body fluids and skin properties change between days and/or within individual days for a single subject. New measurements of information related to the therapy of subject 12 taken by subject information module 36 enables quantification of the impact of the electrical stimulation applied by system 10 to subject 12 in particular, and/or to the specific condition of subject 12 at the time of therapy.

In one embodiment, to obtain further information related to the impact of the electrical stimulation provided to subject 12 by system 10, subject information module 36 is configured to receive user inputs from subject 12 through user interface 18. These inputs include selection and/or entry by subject 12 (or other users) of the impact of the electrical stimulation on subject 12. For example, the inputs may indicate subjective quantification of the impact, such as level of discomfort at the stimulation locations, perceived changes in balance and/or spatial orientation (and/or magnitude or frequency thereof), level of hunger, level of excitement, level of relaxation, level of digestive discomfort (e.g., nausea), travel sickness, sleepiness, dizziness, and/or other subjective quantifications of impact. The inputs may indicate non-subjective quantification of the impact, such as hours of sleep obtained, amount of food consumed, body weight, sleep onset latency, and/or other non-subjective quantifications of impact.

The therapy module 34 is further configured to adjust the parameters of the electrical stimulation provided to subject 12 based on information determined and/or obtained by subject information module 36. This adjustment amounts to a customization of the electrical stimulation to subject 12 based on feedback obtained through direct measurement (e.g. from the output signal of sensor 22) and/or user input. The adjustment made by therapy module 34 changes the parameters of electrical stimulation in order to provide an intended impact on the vestibular system (and/or related systems) dictated by the therapy regime. For example, therapy module 34 may compare an intended impact on the vestibular system dictated by the therapy regime with an apparent or actual impact on the vestibular system, as indicated by the information received from subject information module 36. Based on this comparison, therapy module 34 may adjust one or more parameters of the electrical stimulation of the therapy regime to bring the apparent or actual impact closer to the intended impact.

In one embodiment, the inclusion of separate subject contact surfaces 28 in first subject stimulation interface 20 and/or second subject stimulation interface 30 enables the adjustment made by therapy module 34 to the therapy regime to account for individual anatomy, electrical properties, and/or sensitivity of subject 12. In particular, in adjusting the parameters of the electrical stimulation of the therapy regime, therapy module 34 adjusts one or more of the parameters of the electrical stimulation administered at the individual subject contact surfaces 28 relative to each other. For example, one or more of an amplitude, frequency of modulation, phase of modulation, polarity, pulse shape of modulation, pulse width of modulation, pulse pause of modulation, pulse train of modulation, and/or other parameters of the electrical stimulation applied to subject 12 through a first subject contact surface 28 in the first set of subject contact surfaces 28 may be adjusted without impacting the same parameter(s) of electrical stimulation applied to subject 12 through a second subject contact surface 28 in the first set of subject contact surfaces 28. As another example, the parameter(s) of electrical stimulation applied through the first subject contact surface 28 and the second subject contact surface 28 may both be adjusted in the therapy regime, but by different magnitudes, in different directions, and/or with other differences.

This level of customizability in adjusting the parameters of electrical stimulation applied to the external skin of subject 12 to stimulate the vestibular system may be an enhancement over conventional approaches in which a single electrode or electrode pair has been used to provide a uniform stimulation to subject 12. In particular, the aforementioned conventional approaches have not permitted different locations on the skin of subject 12 receiving electrical stimulation to be addressed individually. Instead, any changes to the applied electrical stimulation have been made to uniformly to the single profile of electrical stimulation being applied to subject 12 on each side of the head.

Figure 2:
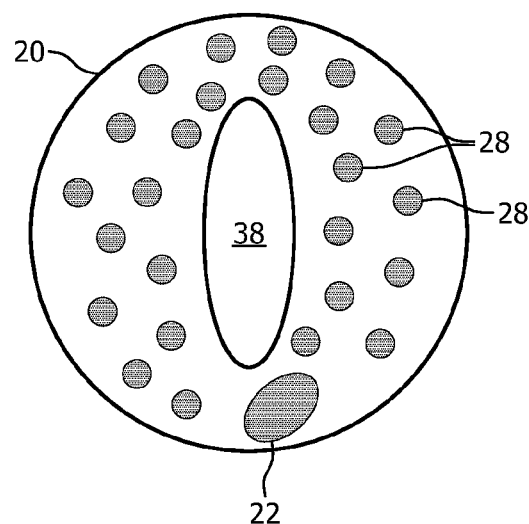
FIG. 2 illustrates a subject stimulation interface, in accordance with one or more embodiments of the invention.

FIG. 2 illustrates an exemplary embodiment of first subject stimulation interface 20. In the embodiment illustrated in FIG. 2, first subject stimulation interface 20 is formed as a single unit carrying a plurality (e.g., three or more) subject contact surfaces 28 included in the first set of subject contact surfaces 28. As has been discussed above, individual ones of subject contact surfaces 28 may be controlled to deliver electrical stimulation having different parameter profiles. For example, the amplitude, frequency of modulation, phase of modulation, polarity, pulse shape of modulation, pulse width of modulation, pulse pause of modulation, pulse train of modulation, and/or other parameters of the electrical stimulation applied through subject contact surfaces 28 can be controlled on a surface by surface basis.

In the embodiment shown in FIG. 2, first subject stimulation interface 20 further carries sensor 22. The sensor 22 may contact the skin of the subject at or near the locations at which the first set of subject contact surfaces 28 contact the skin of the subject. The sensor 22 is configured to generate an output signal related to the electrical properties of the skin and/or the contact between first subject stimulation interface 20 and the skin. Such properties may include one or more of resistance, capacitance, impedance, and/or other electrical properties. Output signals conveying information related to these and/or other electrical parameters of the skin and/or body tissues of subject 12 may be generated by subject contact surfaces 28. The sensor 22 may include a source of electromagnetic radiation and/or a photodetector to take optical measurements of physiological functions of subject 12. For example, optical measurements may be taken of oxygenation, hydration, respiration, cardiovascular function(s), and/or other physiological functions. The optical source and/or photodetector may or may not contact the subject.

The first subject stimulation interface 20 further includes an opening 38. The opening 38 is configured to receive the ear of the subject therethrough, such that when first subject stimulation interface 20 is installed for delivery of therapy to the subject, first subject stimulation interface 20 surrounds the ear of the subject.

Figure 3:
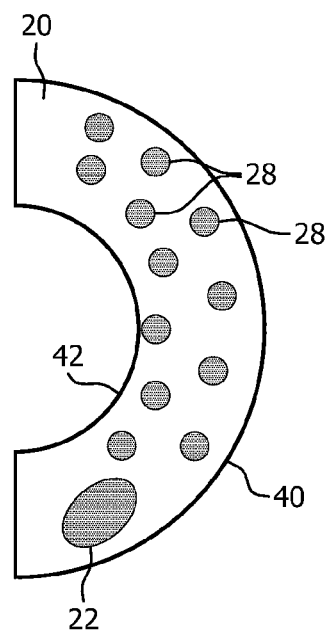
FIG. 3 illustrates a subject stimulation interface, in accordance with one or more embodiments of the invention.

FIG. 3 illustrates an exemplary embodiment of first subject stimulation interface 20. In the embodiment illustrated in FIG. 3, first subject stimulation interface 20 includes the first set of subject contact surfaces 28 and the sensor 22, as was discussed above with the embodiment shown in FIG. 2. In the embodiment shown in FIG. 3, first subject stimulation interface 20 has a curved, or generally arcuate, shape to facilitate installment of first subject stimulation interface 20 around the back (or the front) of the ear of the subject. In particular, first subject stimulation interface 20 bounded by a first curved boundary 40 and a second curved boundary 42 having a smaller radius and/or tighter curvature than first curved boundary 40. When installed on the subject, the second curved boundary 42 is positioned adjacent to the back (or the front) of the ear of the subject.

Figure 4:
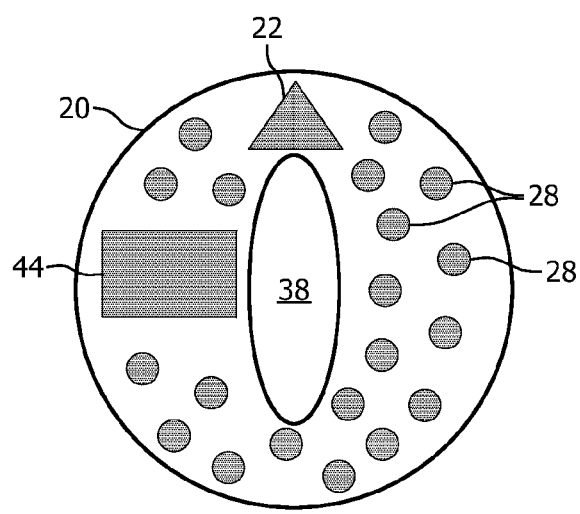
FIG. 4 illustrates a subject stimulation interface, in accordance with one or more embodiments of the invention.

FIG. 4 illustrates an exemplary embodiment of first subject stimulation interface 20. In the embodiment illustrated in FIG. 4, first subject stimulation interface 20 carries the first set of subject contact surfaces 28, sensor 22, a pulse generator 44, and/or other components. The sensor 22 is configured to generate an output signal conveying information related to the impact of the electrical stimulation delivered through subject contact surfaces 28 on the vestibular system of the subject. As a non-limiting example, sensor 22 may generate an output signal conveying information related to the position and/or motion of the subject. For instance, sensor 22 may include an accelerometer, a digital compass, a gyroscope, and/or other sensors.

The pulse generator 44 is configured to perform at least some of the functionality attributed above with respect to power source 14 and/or processor 24 (shown in FIG. 1 and described above). For example, pulse generator 44 is configured to provide electrical stimulation to subject contact surfaces 28 individually in accordance with a therapy regime. In order to enhance the form factor, simplicity, reliability, and/or cost of pulse generator 44, some of the functionality attributed above to processor 24 (shown in FIG. 1 and described above) may be omitted from the capabilities of pulse generator 44. If this is the case, some or all of the functionality of processor 24 omitted from pulse generator 44 may be provided by one or more processors not carried by first subject stimulation interface 20 that are operatively linked with pulse generator 44. The operative link may be accomplished, for example, via a wired or wireless communication medium, and/or may include a docking station in which first subject stimulation interface 20 is docked when not in use.

Figure 5:
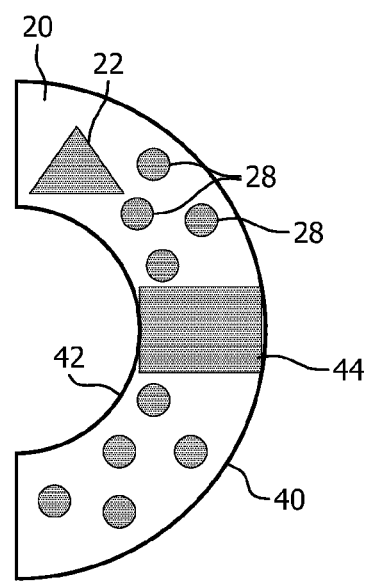
FIG. 5 illustrates a subject stimulation interface, in accordance with one or more embodiments of the invention.

FIG. 5 illustrates an exemplary embodiment of first subject stimulation interface 20. In the embodiment illustrated in FIG. 5, first subject stimulation interface 20 includes the sensor 22 and pulse generator 44 discussed above with respect to FIG. 4. In the embodiment shown in FIG. 5, first subject stimulation interface 20 has the same general shape as the embodiment of first subject stimulation interface 20 shown in FIG. 3 and described above.

It will be appreciated that the configurations of the components of system 10 shown in FIGS. 1-5 are not intended to be limiting. For example, more or fewer components of system 10 may be carried by first subject stimulation interface 20 and/or second subject stimulation interface 30. As another example, power source 14, electronic storage 16, user interface 18, and processor 24 may be disposed within a single device in operative communication with first subject stimulation interface 20, second subject stimulation interface 30, and/or sensor 22. Other configurations are also contemplated.

Figure 6:
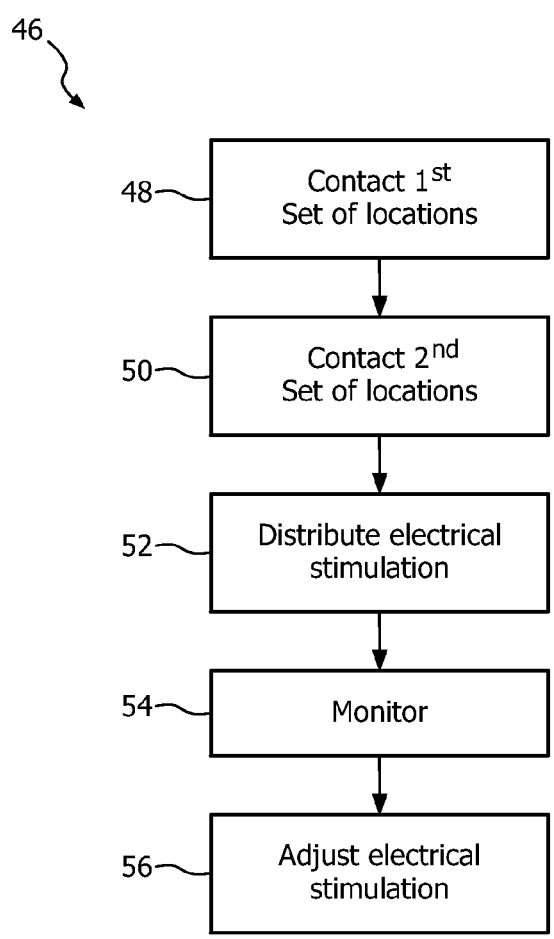
FIG. 6 illustrates a method of administering vestibular stimulation to a subject, according to one or more embodiments of the invention.

FIG. 6 illustrates a method 46 of administering vestibular stimulation to a subject. The operations of method 46 presented below are intended to be illustrative. In some embodiments, method 46 may be accomplished with one or more additional operations not described, and/or without one or more of the operations discussed. Additionally, the order in which the operations of method 46 are illustrated in FIG. 6 and described below is not intended to be limiting.

In some embodiments, method 46 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 46 in response to instructions stored electronically on an electronic storage medium. The one or more processing devices may include one or more devices configured through hardware, firmware, and/or software to be specifically designed for execution of one or more of the operations of method 46.

At an operation 48, the skin of the subject is contacted at a first set of locations at or near a first ear of the subject. The first set of locations may include locations at or near the back of the first ear and/or surrounding the first ear. The first set of locations is arranged such that distribution of electrical stimulation to the first set of locations impacts the vestibular system of the subject on the same side of the subject as the first ear. The skin of the subject is contacted at the first set of locations by a first set of subject contact surfaces. In one embodiment, the first set of subject contact surfaces are similar to or the same as subject contact surfaces 28 (shown in FIGS. 1-5 and described above). The first set of subject contact surfaces may be carried by a first subject stimulation interface similar to or the same as first subject stimulation interface 20 (shown in FIGS. 1-5 and described above).

At an operation 50, the skin of the subject is contacted at a second set of locations at or near a second ear of the subject. The second set of locations may include locations at or near the back of the second ear and/or surrounding the second ear. The second set of locations are arranged such that distribution of electrical stimulation to the second set of locations impacts the vestibular system of the subject on the same side of the subject as the second ear. The skin of the subject is contacted at the second set of locations by a second set of subject contact surfaces. The second set of subject contact surfaces are similar to or the same as subject contact surfaces 28 (shown in FIG. 1 and described above). The second set of subject contact surfaces may be carried by a second subject stimulation interface similar to or the same as second subject stimulation interface 30 (shown in FIG. 1 and described above).

At an operation 52, electrical stimulation is distributed to the first and/or second set of locations through the first and/or second set of subject contact surfaces. The electrical stimulation is distributed through the first set of subject contact surfaces such that within the first set of subject contact surfaces the parameters of the electrical stimulation vary between the subject contact surfaces. Similarly, the electrical stimulation is distributed through the second set of subject contact surfaces such that within the second set of subject contact surfaces the parameters of the electrical stimulation vary between the subject contact surfaces. The electrical stimulation is distributed at operation 52 in accordance with a therapy regime that the distribution of electrical stimulation in a coordinated manner to have a therapeutic impact on the vestibular system of the subject. The coordination of the electrical stimulation may include coordinating the distribution between the first set of subject contact surfaces and the second set of contact surfaces in an orchestrated manner. For example to create a rocking sensation of 1 Hz, the first set of subject contact surfaces may be activated for 0.5 sec and then the second set of subject contact surfaces may be activated for 0.5 sec. In one embodiment, operation 52 is performed by one or more processors similar to or the same as processor 24 (shown, at least partially, in FIGS. 1, 4, and 5, and described above).

At an operation 54, the communication of electrical stimulation to the skin of the subject and/or the impact on the vestibular system of the distributed electrical stimulation is monitored. Monitoring the communication of electrical stimulation to the skin of the subject may include determining one or more electrical properties of the skin of the subject, one or more properties of the contacts with the skin of the subject, and/or other properties. For example, monitoring the communication of electrical stimulation to the skin of the subject may include monitoring one or more of resistance, capacitance, impedance, and/or other electrical properties. Monitoring the impact on the vestibular system of the distributed electrical stimulation may include monitoring one or more physiological functions of the subject. The one or more physiological functions may include one or more of balance, perceived spatial orientation, a vascular tone, a core temperature, a metabolic function, a pulse shape, a galvanic skin response, a heart rate variability, a baroreceptor sensitivity, a body weight, a muscle sympathetic nerve activation, a pupillary dilation, peristaltic movement of materials through the patient's digestive system, a blood pressure, oxygenation, hydration, respiration, and/or other physiological functions. The monitoring performed at operation 54 may include automatically obtaining and/or analyzing information (e.g., with a sensor and/or a processor), and/or may include receiving user inputs. In one embodiment, operation 54 is performed by a sensor, a processor, and/or a user interface similar to sensor 22, subject contact surfaces 28, processor 24, and/or user interface 18, respectively (shown in FIG. 1 and described above).

At an operation 56, one or more parameters of the electrical stimulation distributed to the first set and/or the second set of locations on the skin of the subject are adjusted based on the monitoring performed at operation 54. The adjustment of the parameter may include adjusting the electrical stimulation distributed to individual locations through subject contact surfaces individually from each other. This results in the adjustment of the parameters of electrical stimulation delivered through at least one subject contact surface in the first set of subject contact surfaces relative to the parameters of electrical stimulation delivered through at least one other subject contact surface in the first set of subject contact surfaces. This granular adjustment of parameters of electrical stimulation may enhance the customizability of the therapy provided by method 46 to the individual subject. In one embodiment, operation 56 is performed by a processor similar to or the same as processor 24 (shown at least in part in FIGS. 1, 4, and 5 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system configured to stimulate the vestibular system of a subject and affect balance of the subject, the system comprising:
   a first set of subject contact surfaces including at least three subject contact surfaces, wherein:
      the subject contact surfaces in the first set of subject contact surfaces are spatially distinct from each other, and wherein the subject contact surfaces are configured to be installed on the skin of the subject at or near a first ear of the subject in electrical contact with the skin of the subject such that delivery of electrical stimulation to the first set of contact surfaces provides the electrical stimulation to the vestibular system of the subject on the same side of the subject as the first ear, the electrical stimulation being characterized by one or more sets of electrical settings; and
   wherein at least one of the subject contact surfaces in the first set of subject contact surfaces is configured to generate output signals conveying information related to impact of the electrical stimulation on the balance of the subject; and
   a processor configured via computer-readable instructions that cause the processor to:
      determine a balance parameter of the subject based on the output signals generated by the at least one of the subject contact surfaces in the first set of subject contact surfaces, wherein the balance parameter indicates the impact of the electrical stimulation on the balance of the subject;
      control the delivery of the electrical stimulation to individual ones of the subject contact surfaces in the first set of subject contact surfaces such that at a given moment in time a first electrical stimulation is being delivered to a first subject contact surface in the first set of subject contact surfaces, the first electrical stimulation having a first set of electrical settings, and such that a second electrical stimulation is being delivered to a second subject contact surface in the first set of subject contact surfaces, the second electrical stimulation having a second set of electrical settings; and adjust at least one of the first set of electrical settings of the first electrical stimulation, based on the balance parameter, without impacting the second set of electrical settings.

2. The system of claim 1, wherein the first set of electrical settings of the first electrical stimulation comprise one or more of frequency of modulation, pulse width of modulation, pulse pause of modulation, or pulse shape of modulation.

3. The system of claim 1, wherein the processor is configured to control the delivery of the electrical stimulation in a coordinated manner to have a therapeutic impact on the vestibular system.

4. The system of claim 1, further comprising a second set of subject contact surfaces including at least three subject contact surfaces, wherein the subject contact surfaces in the second set of subject contact surfaces are spatially distinct from each other, wherein the subject contact surfaces in the second set of subject contact surfaces are configured to be installed on the skin of the subject at or near a second ear of the subject in electrical contact with the skin of the subject such that delivery of a given electrical stimulation to the second set of contact surfaces provides the given electrical stimulation to the vestibular system of the subject on the same side of the subject as the second ear, the given electrical stimulation being characterized by one or more sets of electrical settings; and wherein at least one of the subject contact surfaces in the second set of subject contact surfaces is configured to generate output signals conveying information related to impact of the given electrical stimulation on the balance of the subject, and wherein the processor is further configured to:

determine a second balance parameter of the subject based on the output signals generated by the at least one of the subject contact surfaces in the second set of subject contact surfaces, wherein the second balance parameter indicates the impact of the given electrical stimulation on the balance of the subject;

control delivery of the given electrical stimulation to the subject contact surfaces in the second set of subject contact surfaces such that at a second given moment in time a third electrical stimulation is being delivered to a first subject contact surface in the second set of subject contact surfaces, the third electrical stimulation having a third set of electrical settings of electrical stimulation, and such that a fourth electrical stimulation is being delivered to a second subject contact surface in the second set of subject contact surfaces, the fourth electrical stimulation having a fourth set of electrical settings; and adjust at least one of the third set of electrical settings of the third stimulation based on the second balance parameter without impacting the fourth set of set of electrical settings.

5. The system of claim 1, further comprising a sensor configured to generate an output signal conveying information related to delivery of electrical stimulation between at least one of the subject contact surfaces in the first set of subject and the skin of the subject, and wherein the processor is further configured to adjust at least one of the first set of electrical settings of the first electrical stimulation based on the output signal generated by the sensor.

6. A method of stimulating the vestibular system of a subject and affecting balance of the subject, the method comprising:

contacting the skin of the subject through a first set of subject contact surfaces including at least three subject contact surfaces, wherein the subject contact surfaces in the first set of subject contact surfaces are spatially distinct from each other, and wherein the subject contact surfaces contact the skin of the subject at or near a first ear of the subject such that delivery of electrical stimulation to the first set of contact surfaces provides the electrical stimulation to the vestibular system of the subject on the same side of the subject as the first ear, the electrical stimulation being characterized by one or more sets of electrical settings;

generating, by at least one of the subject contact surfaces in the first set of subject contact surfaces, output signals conveying information related to impact of the electrical stimulation on the balance of the subject;

determining a balance parameter of the subject based on the output signals generated by the at least one of the subject contact surfaces in the first set of subject contact surfaces, wherein the balance parameter indicates the impact of the electrical stimulation on the balance of the subject;

delivering a first electrical stimulation to a first subject contact surface in the first set of subject contact surfaces, the first electrical stimulation having a first set of electrical settings;

delivering a second electrical stimulation to a second subject contact surface in the first set of subject contact surfaces, the second electrical stimulation having a second set of electrical settings; and adjusting at least one of the first set of electrical settings of the first electrical stimulation, based on the balance parameter, without impacting the second set of electrical settings.

7. The method of claim 6, wherein the first set of settings of the first electrical stimulation comprise one or more of frequency of modulation, pulse width of modulation, pulse pause of modulation, or pulse shape of modulation.

8. The method of claim 6, wherein delivering electrical stimulation to the first set of subject contact surfaces is performed in a coordinated manner to have a therapeutic impact on the vestibular system.

9. The method of claim 6, further comprising:

contacting the skin of the subject through a second set of subject contact surfaces including at least three subject contact surfaces, wherein the subject contact surfaces in the second set of subject contact surfaces are spatially distinct from each other, wherein the subject contact surfaces in the second set of subject contact surfaces contact the skin of the subject at or near a second ear of the subject such that delivery of a given electrical stimulation to the second set of contact surfaces provides the given electrical stimulation to the vestibular system of the subject on the same side of the subject as the second ear, the given electrical stimulation being characterized by one or more sets of electrical settings;

generating, by at least one of the subject contact surfaces in the second set of subject contact surfaces, output signals conveying information related to impact of the given electrical stimulation on the balance of the subject;

determining a second balance parameter of the subject based on the output signals generated by the at least one of the subject contact surfaces in the second set of subject contact surfaces, wherein the second balance parameter indicates the impact of the given electrical stimulation on the balance of the subject;

delivering a third electrical stimulation to a first subject contact surface in the second set of subject contact surfaces, the third electrical stimulation having a third set of electrical settings of electrical stimulation;

delivering a fourth electrical stimulation to a second subject contact surface in the second set of subject contact surfaces, the fourth electrical stimulation having a fourth set of electrical settings; and adjusting at least one of the third set of electrical settings of the third electrical stimulation, based on the second balance parameter, without impacting the fourth set of electrical settings.

10. The method of claim 6, further comprising:

generating an output signal by monitoring the delivery of the electrical stimulation between at least one of the subject contact surfaces in the first set of subject contact surfaces and the skin of the subject; and adjusting at least one of the first set of electrical settings of the first electrical stimulation based on the generated output signal.

11. A system configured to stimulate the vestibular system of a subject and affect balance of the subject, the system comprising:

first means for contacting the skin of the subject including at least three subject contact surfaces, wherein the subject contact surfaces in the first means contacts the skin of the subject at locations that are spatially distinct from each other and are at or near a first ear of the subject such that delivery of electrical stimulation to the locations contacted by the first means provides the electrical stimulation to the vestibular system of the subject on the same side of the subject as the first ear, the electrical stimulation being characterized by one or more sets of electrical settings;

means for generating output signals conveying information related to impact of the electrical stimulation on the balance of the subject;

means for determining a balance parameter of the subject based on the output signals generated by the means for generating, wherein the balance parameter indicates the impact of the electrical stimulation on the balance of the subject; and means for delivering electrical stimulation to individual ones of the locations on the skin of the subject contacted by the first means such that at a given moment in time a first electrical stimulation is being delivered to a first subject contact surface, the first electrical stimulation having a first set of electrical settings, and such that a second electrical stimulation is being delivered to a second subject contact surface, the second electrical stimulation having a second set of electrical settings, wherein the means for delivering electrical stimulation is configured to adjust at least one of the first set of electrical settings of the first electrical stimulation, based on the balance parameter, without impacting the second set of electrical settings.

12. The system of claim 11, wherein the set of electrical settings of the first electrical stimulation comprise one or more of frequency of modulation, pulse width of modulation, pulse pause of modulation, or pulse shape of modulation.

13. The system of claim 11, wherein delivering electrical stimulation to the locations on the skin of the subject contacted by the first means is performed in a coordinated manner to have a therapeutic impact on the vestibular system.

14. The system of claim 11, further comprising:

second means for contacting the skin of the subject including at least three subject contact surfaces, wherein the second means contacts the skin of the subject at locations that are spatially distinct from each other and are at or near a second ear of the subject such that delivery of a given electrical stimulation to the locations on the skin of the subject contacted by the second means provides the given electrical stimulation to the vestibular system of the subject on the same side of the subject as the second ear, the given electrical stimulation being characterized by one or more sets of electrical settings;

means for generating output signals conveying information related to impact of the given electrical stimulation on the balance of the subject;

means for determining a balance parameter of the subject based on the output signals generated by the means for generating, wherein the balance parameter indicates the impact of the given electrical stimulation on the balance of the subject; and means for the given delivering electrical stimulation to the locations contacted by the second means such that at a given moment in time a third electrical stimulation is being delivered to a first subject contact surface of the second means, the third electrical stimulation having a third set of electrical settings, and such that a fourth electrical stimulation is being delivered to a second subject contact surface of the second means, the fourth electrical stimulation having a fourth set of electrical settings, wherein the second means for delivering electrical stimulation is configured to adjust at least one of the third set of settings of the third electrical stimulation, based on the balance parameter, without impacting the fourth set of electrical settings.

15. The system of claim 11, further comprising:

means for generating an output signal by monitoring the delivery of the electrical stimulation between the first means and at least one location on the skin of the subject; and means for adjusting at least one of the first set of electrical settings of the first electrical stimulation based on the generated output signal.

* * * * *